(12) United States Patent
Matsushima et al.

(10) Patent No.: US 7,521,596 B2
(45) Date of Patent: Apr. 21, 2009

(54) METHOD FOR CONTROLLING WEEDS

(75) Inventors: Yutaka Matsushima, Kobe (JP); Akitsu Nagasawa, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 376 days.

(21) Appl. No.: 11/129,574

(22) Filed: May 16, 2005

(65) Prior Publication Data

US 2006/0009361 A1 Jan. 12, 2006

(30) Foreign Application Priority Data

May 17, 2004 (JP) ............................. 2004-146019
Mar. 11, 2005 (JP) ............................. 2005-068714

(51) Int. Cl.
*C12N 15/82* (2006.01)
(52) U.S. Cl. ...................................... 800/288; 800/300
(58) Field of Classification Search ....................... None
See application file for complete search history.

(56) References Cited

U.S. PATENT DOCUMENTS

| | | | |
|---|---|---|---|
| 4,940,838 | A | 7/1990 | Schilperoort et al. |
| 5,179,013 | A | 1/1993 | Matsuoka et al. |
| 5,204,253 | A | 4/1993 | Sanford et al. |
| 5,212,296 | A | 5/1993 | Dean et al. |
| 5,231,019 | A | 7/1993 | Paszkowski et al. |
| 5,349,127 | A | 9/1994 | Dean et al. |
| 5,717,084 | A | 2/1998 | Herrera-Estrella et al. |
| RE36,449 | E | 12/1999 | Lebrun et al. |
| 6,121,512 | A | 9/2000 | Siminszky et al. |
| 6,613,961 | B1 | 9/2003 | Ohkawa et al. |
| 2005/0084859 | A1 * | 4/2005 | Nakajima et al. .............. 435/6 |

FOREIGN PATENT DOCUMENTS

| | | |
|---|---|---|
| JP | 9-252778 A | 9/1997 |
| WO | WO 00/00585 A2 | 1/2000 |
| WO | WO 03/040370 A1 * | 5/2003 |

OTHER PUBLICATIONS

Duke et al., "Porphyric Pesticides: Chemistry, Toxicology, and Pharmaceutical Applications," ACS Symposium Series, 1994, American Chemical Society, Washington, D.C.
Duke et al., "Protoporphyrinogen Oxidase-Inhibiting Herbicides," Weed Science, Jul.-Sep. 1991, pp. 465-473, vol. 39, No. 3.
Fromm, et al., "Inheritance and Expression of Chimeric Genes in the Progeny of Transgenic Maize Plants," Biotechnology, Sep. 1990, pp. 833-839, vol. 8.
Hybridization of Radiolabeled Probes to Nucleic Acids Immobilized on Nitrocellulose Filters or Nylon Membranes, Molecular Cloning, A Laboratory Manual, Second Edition, 1989, pp. 9.52-9.55, Cold Spring Harbor Laboratory Press, USA.
Kramer et al., "The Gapped Duplex DNA Approach to Oligonucleotide-directed Mutation Construction," Nucleic Acids Research, 1984, pp. 9441-9456, vol. 12, No. 24, IRL Press Limited, England.
Lerner et al., "Localized Random Polymerase Chain Reaction Mutagenesis, Methods in Molecular Biology," 1994, pp. 97-112, vol. 31, Humana Press, Inc., Totowa, NJ.
Lipman et al., "Rapid and Sensitive Protein Similarity Searches," Science, Mar. 22, 1985, pp. 1435-1441, vol. 227.
Matringe et al., "Protoporphyrinogen Oxidase Inhibition by Three Peroxidizing Herbicides: Oxadiazon, LS 82-556 and M&B 39279," FEBS Letters, Mar. 1989, pp. 35-38, vol. 245, No. 1, 2, Elsevier Science Publishers B.V.
Murashige et al., "A Revised Medium for Rapid Growth and Bio Assays with Tobacco Tissue Cultures," Physiol. Plant., 1962, vol. 15, No. 3, pp. 473-497, Copenhagen.
Nandihalli et al., "Quantitative Structure-Activity Relationships of Protoporphyrinogen Oxidase-Inhibiting Diphenyl Ether Herbicides," Pesticide Biochem. & Physiol., 1992, pp. 193-211, vol. 43, Academic Press, Inc.
Pearson et al., "Improved Tools for Biological Sequence Comparison," Proc. Natl. Acad. Sci. USA, Apr. 1988, pp. 2444-2448, vol. 85.
Thompson et al., Clustal W: Improving the Sensitivity of Progressive Multiple Sequence Alignment Through Sequence Weighting, Position-specific Gap Penalities and Weight Matrix Choice, Nucleic Acids. Research, 1994, pp. 4673-4680, vol. 22, No. 22, Oxford University Press.
Sambrook et al., Molecular Cloning, A Laboratory Manual, Second Edition, 1989, Book 1, pp. xi-xxxviii, Cold Spring Harbor Laboratory Press, USA.
Yanase et al., "Porphyrin Synthesis Involvement in Diphenyl Ether-like Mode of Action of TNPP-Ethyl, a Novel Phenylpyrazole Herbicide," Pesticide Biochem. & Physio., 1989, pp. 70-80, vol. 35, Academic Press, Inc.
Werck-Reichhart et al., "Cytochromes P450 for engineering herbicide tolerance" Trend in Plant Science, Mar. 2000, pp. 116-123, vol. 5(3), Elsevier Science Ltd, U.S.A.
Ohkawa et al., "The use of cytochrome P450 genes to introduce herbicide tolerance in crops: a review", Pesticide Science, 1999, pp. 867-874, vol. 55, Society of Chemical Industry, U.S.A.

* cited by examiner

*Primary Examiner*—David H Kruse
(74) *Attorney, Agent, or Firm*—Foley & Lardner LLP

(57) ABSTRACT

The present invention provides a method for controlling weeds comprising a step of applying one or more compounds to a cultivation area of a plant, to which a gene of cytochrome P450 showing activity of metabolizing a protoporphyrinogen IX oxidase inhibitory-type herbicidal compound has been introduced, wherein said compound to be applied to said area is selected from the group consisting of:

(1) flufenpyr-ethyl,
(2) 2-[4-chloro-2-fluoro-5-(2-propynyloxy)phenyl]-4-methy-5-(trifluoromethyl)-3(2H)-pyridazinone,
(3) carfentrazone-ethyl, and
(4) sulfentrazone; and the like.

6 Claims, 2 Drawing Sheets

```
                          SEQUENCE LISTING

<160> NUMBER OF SEQ ID NOS: 4

<210> SEQ ID NO 1
<211> LENGTH: 398
<212> TYPE: PRT
<213> ORGANISM: Streptomyses steffisburgensis IFO13446T

<400> SEQUENCE: 1

Met Ser Asp Thr Thr Ala Pro Val Ala Phe Pro Gln Ser Arg Thr Cys
  1               5                  10                  15

Pro Tyr His Pro Pro Ala Ala Tyr Glu Pro Leu Arg Ala Glu Arg Pro
             20                  25                  30

Leu Thr Arg Ile Thr Leu Phe Asp Gly Arg Glu Ala Trp Leu Val Ser
         35                  40                  45

Gly His Ala Thr Ala Arg Ala Leu Leu Ala Asp Pro Arg Leu Ser Ser
     50                  55                  60

Asp Arg Asp Arg Pro Gly Phe Pro Ala Pro Thr Ala Arg Phe Ala Gly
 65                  70                  75                  80

Ile Arg Asn Arg Arg Thr Ala Leu Leu Gly Val Asp Asp Pro Glu His
                 85                  90                  95

Arg Val Gln Arg Arg Met Val Ala Gly Asp Phe Thr Leu Lys Arg Ala
            100                 105                 110

Ala Gly Leu Arg Pro Arg Ile Gln Arg Ile Val Asp Arg Arg Leu Asp
        115                 120                 125

Ala Met Ile Ala Gln Gly Pro Pro Ala Asp Leu Val Ser Ser Phe Ala
    130                 135                 140

Leu Pro Val Pro Ser Met Val Ile Cys Ala Leu Leu Gly Val Pro Tyr
145                 150                 155                 160

Ala Asp His Asp Phe Phe Glu Thr Gln Ser Arg Arg Leu Leu Arg Gly
                165                 170                 175
```

Pro Gln Thr Ala Asp Val Met Asp Ala Arg Ala Arg Leu Asp Glu Tyr
            180                 185                 190

Phe Gly Glu Leu Ile Asp Arg Lys Arg Lys Glu Pro Gly Ala Gly Leu
            195                 200                 205

Leu Asp Asp Leu Val Gln Arg Gln Leu Arg Asp Gly Ala Leu Asp Arg
            210                 215                 220

Glu Gly Leu Ile Ala Leu Ala Leu Ile Leu Val Ala Gly His Glu
225                 230                 235                 240

Thr Thr Ala Asn Met Ile Ser Leu Gly Thr Phe Thr Leu Leu Gln His
                245                 250                 255

Pro Glu Arg Leu Ala Glu Leu Arg Ala Asp Pro Arg Leu Leu Pro Ala
            260                 265                 270

Ala Val Glu Glu Leu Met Arg Met Leu Ser Ile Ala Asp Gly Leu Leu
            275                 280                 285

Arg Leu Ala Val Glu Asp Ile Glu Val Ala Gly Thr Thr Ile Arg Lys
            290                 295                 300

Gly Asp Gly Val Val Phe Leu Thr Ser Val Ile Asn Arg Asp Glu Thr
305                 310                 315                 320

Val Tyr Pro Glu Pro Asp Thr Leu Asp Trp His Arg Ser Ala Arg His
                325                 330                 335

His Val Ala Phe Gly Phe Gly Ile His Gln Cys Leu Gly Gln Asn Leu
            340                 345                 350

Ala Arg Ala Glu Leu Glu Ile Ala Leu Trp Thr Leu Phe Asp Arg Leu
            355                 360                 365

Pro Thr Leu Arg Leu Ala Ala Pro Ala Glu Glu Ile Ala Phe Lys Pro
            370                 375                 380

Gly Asp Thr Ile Gln Gly Met Leu Glu Leu Pro Val Thr Trp
385                 390                 395

<210> SEQ ID NO 2
<211> LENGTH: 398
<212> TYPE: PRT
<213> ORGANISM: Streptomyses roseorubens IFO13682T

<400> SEQUENCE: 2

Met Thr Asp Thr Thr Ala Pro Val Ala Phe Pro Gln Ser Arg Thr Cys
1               5                   10                  15

Pro Tyr His Pro Pro Ala Ala Tyr Glu Pro Leu Arg Ala Glu Arg Pro
                20                  25                  30

Leu Thr Arg Ile Thr Leu Phe Asp Gly Arg Glu Ala Trp Leu Val Ser
            35                  40                  45

Gly His Ala Thr Ala Arg Ala Leu Leu Ala Asp Pro Arg Leu Ser Ser
        50                  55                  60

Asp Arg Asp Arg Pro Gly Phe Pro Thr Pro Thr Ala Arg Phe Ala Gly
65                  70                  75                  80

Ile Arg Asn Arg Arg Thr Ala Leu Leu Gly Val Asp Asp Pro Glu His
                85                  90                  95

Arg Ala Gln Arg Arg Met Val Val Gly Asp Phe Thr Leu Lys Arg Ala
            100                 105                 110

Ala Ala Leu Arg Pro Arg Ile Gln Arg Ile Val Asp Glu Arg Leu Asp
        115                 120                 125

Ala Met Ile Ala Gln Gly Pro Pro Ala Asp Leu Val Ser Ala Phe Ala
    130                 135                 140

Leu Pro Val Pro Ser Met Val Ile Cys Ala Leu Leu Gly Val Pro Tyr

```
            145                 150                 155                 160
Ala Asp His Asp Phe Phe Glu Ala Gln Ser Arg Arg Leu Leu Arg Gly
                165                 170                 175

Pro Gly Thr Ala Asp Val Gln Asp Ala Arg Ser Arg Leu Glu Glu Tyr
                180                 185                 190

Phe Gly Glu Leu Ile Asp Arg Lys Arg Glu Asp Pro Gly Thr Gly Leu
                195                 200                 205

Leu Asp Asp Leu Val Gln Arg Gln Pro Gly Asp Gly Gly Pro Asp Arg
                210                 215                 220

Glu Gly Leu Ile Ala Met Ala Leu Ile Leu Leu Val Ala Gly His Glu
225                 230                 235                 240

Thr Thr Ala Asn Met Ile Ser Leu Gly Thr Phe Thr Leu Leu Gln His
                245                 250                 255

Pro Glu Arg Leu Ala Glu Leu Arg Ala Asp Ser Glu Val Met Pro Ala
                260                 265                 270

Ala Val Glu Glu Leu Met Arg Leu Leu Ser Ile Ala Asp Gly Leu Leu
                275                 280                 285

Arg Ile Ala Val Glu Asp Val Glu Val Ala Gly Thr Thr Ile Arg Ala
                290                 295                 300

Gly Glu Gly Val Val Phe Ala Thr Ser Val Ile Asn Arg Asp Glu Thr
305                 310                 315                 320

Val Phe Ala Glu Pro Asp Thr Leu Asp Trp Ser Arg Pro Ala Arg His
                325                 330                 335

His Val Ala Phe Gly Phe Gly Ile His Gln Cys Leu Gly Gln Asn Leu
                340                 345                 350

Ala Arg Ala Glu Leu Glu Ile Ala Leu Gly Thr Leu Phe Gly Arg Leu
                355                 360                 365

Pro Thr Leu Arg Leu Ala Ala Pro Pro Asp Glu Ile Pro Phe Lys Pro
                370                 375                 380

Gly Asp Thr Ile Gln Gly Met Leu Glu Leu Pro Val Thr Trp
385                 390                 395

<210> SEQ ID NO 3
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 3
aggctttcat ctgatcgtga cagac                                          25

<210> SEQ ID NO 4
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 4
atcagacctt ccctgtctaa tgctc                                          25
```

METHOD FOR CONTROLLING WEEDS

BACKGROUND OF THE INVENTION

1. Field of the Invention

The present invention relates to a method for controling weeds.

2. Description of the Related Art

Protoporphyrinogen IX oxidase inhibitory-type herbicidal compound is contained as an active ingredient in a weed control agent. As a plant on which resistance to the protoporphyrinogen IX oxidase inhibitory-type herbicidal compound has been conferred, for instance, a plant expressing cytochrome P-450 derived from *actinomyces* such that the herbicidal compound is metabolized for inactivation in the plant body (for example, described in International Patent Publication WO0340370 and the like) is known.

SUMMARY OF THE INVENTION

As to the herbicidal compound resistant plant, phytotoxicity from the herbicidal compound tends to occur, since herbicidal action of the herbicidal compound is generally immediate. Therefore, search of more preferable combination with the herbicidal compound used for the plant has been made.

The present invention provides, 1. a method for controlling weeds comprising a step of applying one or more compounds to a cultivation area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced (hereinafter, said DNA may be referred to the present DNA, and said plant may be referred to the present plant),
   wherein said compound to be applied to said area is a protoporphyrinogen IX oxidase inhibitory-type herbicidal compound and selected from the group consisting of:
   (1) flufenpyr-ethyl,
   (2) 2-[4-chloro-2-fluoro-5-(2-propynyloxy)phenyl]-4-methy-5-(trifluoromethyl)-3(2H)-pyridazinone,
   (3) carfentrazone-ethyl, and
   (4) sulfentrazone (hereinafter, said method may be referred to the method for controlling weeds of the present invention, and said compound may be referred to the present herbicidal compound);

2. the method according to the above 1, wherein said cytochrome P450 is cytochrome P450 derived from *actinomyces;*
3. the method according to the above 1, wherein said cytochrome P450 is selected from the group consisting of:
   (1) cytochrome P450 derived from *actinomyces* belonging to *Streptomyces,*
   (2) cytochrome P450 comprising an amino acid sequence having 90% or more sequence homology to the amino acid sequence of SEQ ID NO: 1 or 2,
   (3) cytochrom P450 comprising the amino acid sequence of SEQ ID NO: 1, and
   (4) cytochrome P450 comprising the amino acid sequence of SEQ ID NO: 2;
4. a method for selecting a herbicidal compound resistant plant, said method comprising:
   1) a step of applying or adding one or more compounds to a cultivation area or a culturing area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced,
   wherein said compound to be applied or added to said area is a protoporphyrinogen IX oxidase inhibitory-type herbicidal compound and selected from the group consisting of:
   (1) flufenpyr-ethyl,
   (2) 2-[4-chloro-2-fluoro-5-(2-propynyloxy)phenyl]-4-methy-5-(trifluoromethyl)-3(2H)-pyridazinone,
   (3) carfentrazone-ethyl, and
   (4) sulfentrazone (hereinafter, said method may be referred to the method for selecting of the present invention); and
   2) a step of selecting a plant which has survived the weed control effect of said applied or added compounds;
5. a method for controlling weeds comprising a step of applying flufenpyr-ethyl to a cultivation area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced;
6. a method for controlling weeds comprising a step of applying 2-[4-chloro-2-fluoro-5-(2-propynyloxy)phenyl]-4-methy-5-(trifluoromethyl)-3(2H)-pyridazinone to a cultivation area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced;
7. a method for controlling weeds comprising a step of applying carfentrazone-ethyl to a cultivation area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced; and
8. a method for controlling weeds comprising a step of applying sulfentrazone to a cultivation area of a plant,
   wherein to said plant, a DNA having a nucleotide sequence encoding an amino acid sequence of cytochrome P450 showing activity of metabolizing a protoporphyrinogen IX oxidase inhibitory-type herbicidal compound has been introduced.

Figure 1:
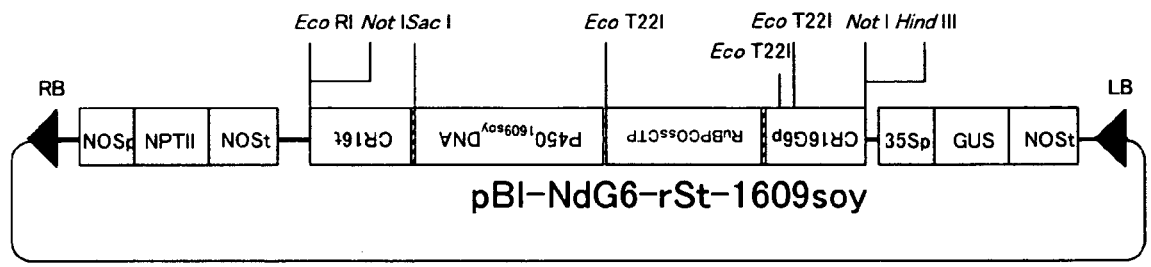
FIG. 1 shows the restriction map of the plasmid pBI-NdG6-rSt-1609soy.

The abbreviations described in the above figures are explained below.

$P450_{1609soy}$DNA: the DNA encoding cytochrom P450 comprising the amino acid sequence of SEQ ID NO: 1.
$P450_{1584soy}$DNA: the DNA encoding cytochrom P450 comprising the amino acid sequence of SEQ ID NO: 2.
RuBPCOssCTP: the nucleotide sequence encoding the chloroplast transit peptide of the small subunit of ribulose-1,5-bisphosphate carboxylase of soybean (cv. Jack).

CR16G6p: DNA in which the nucleotide sequence upstream of restriction site of the restriction enzyme NdeI is removed from the CR16G6 promoter.
CR16t; DNA in which the nucleotide sequence downstream of restriction site of the restriction enzyme ScaI is removed from the CR16 terminator.
NOSp: promoter of the nopaline synthase gene.
NPTII: kanamycin resistance gene.
NOSt: terminator of nopaline synthase gene.
35Sp: 35S promoter of cauliflower mosaic virus.
GUS: β-glucuronidase gene.
RB: the right border sequence of T-DNA.
LB: the left border sequence of T-DNA.
ColE1 ori: the replication origin of plasmid ColE1.
$Amp^r$: the ampicillin resistance gene.
HindIII, EcoRI, BamHI, EcoT221, SacI, NotI: the cleavage sites of the respective restriction enzyme.

DETAILED DESCRIPTION OF THE PREFERRED EXAMPLES

Hereinafter, the present invention will be described in detail.

The "protoporphyrinogen IX oxidase inhibitory-type herbicidal compound" of "cytochrome P450 showing activity of metabolizing a protoporphyrinogen IX oxidase inhibitory-type herbicidal compound" used in the present invention, is a herbicidal compound which is contained as an active ingredient in a composition for weed control and inhibits porphyrin biosynthesis. As the compounds inhibiting porphyrin biosynthesis, for example, there are compounds inhibiting activity of protoporphyrinogen IX oxidase (EC 1.13.11.27, hereinafter may be referred to as PPO) and the like. Specifically for example, as the compounds inhibiting activity of PPO, there are the compounds disclosed in Duke, S. O., Rebeiz, C. A. ACS Symposium Series 559, Porphyric Pesticides, Chemistry, Toxicology, and Pharmaceutical Applications. American Chemical Society, Washington D.C. (1994) and the like. In such herbicidal compounds, various molecular species having different structures are contained (Duke et al., Weed Sci. 39: p 465 (1991); Nandihalli et al., Pesticide Biochem. Physiol. 43: p 193 (1992); Matringe et al., FEBS Lett. 245: p 35 (1989); Yanase, Andoh, Pesticide Biochem. Physiol. 35: p 70 (1989)), there may be, for example, diphenylether:
for instance, chloromethoxynil, biphenox, chloronitrophene (CNP), acifluorfen (i.e. 5-[2-chloro-4-(trifluoromethyl)phenoxy]-2-nitrobenzoic acid and the like) and it's ethyl ester, acifluorfen-sodium, oxyfluorfen (i.e. 2-chloro-1-(3-ethoxy-4-nitrophenoxy) -4-trifluoromethylbenzene), or oxadiazol (for instance, oxadiazon (i.e. 3-[2,4-dichloro-5-(1-methylethoxy)phenyl]-5-(1,1-dimethylethyl)-1,3,4-oxadiazol-2(3H)-one) and the like);

cyclic imide:
for instance, S-23142 (i.e. N-(4-chloro-2-fluoro-5-propargyloxyphenyl)-3,4,5,6-tetrahydrophtalimide and the like), or chlorphthalim (i.e. N-(4-chlorophenyl)-3,4,5,6-tetrahydrophtalimide);

phenylpyrazole:
for instance, TNPP-ethyl (i.e. ethyl 2-[1-(2,3,4-trichlorophenyl)-4-nitropyrazolyl-5-oxy]propionate) and the like;

pyridine derivatives
for instance, LS82-556 (i.e. N3-(1-phenylethyl)-2,6-dimethyl-5-propyonylnicotinamide) and the like;

phenopylate, o-phenylpyrrolidinocarbamate analog of phenopylate, or piperidinocarbamate analog of phenopylate and the like.

As said herbicidal compounds, there may be, specifically for example, a compound of the following formula (I):

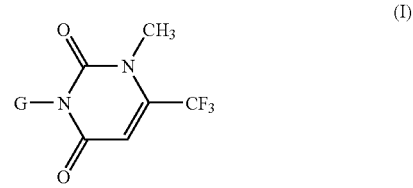

(I)

wherein in formula (I) G represents a group shown in any one of the following G-1 to G-9;

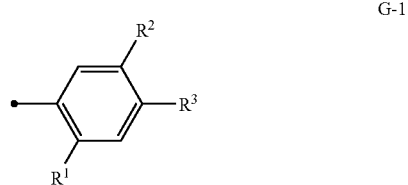

G-1

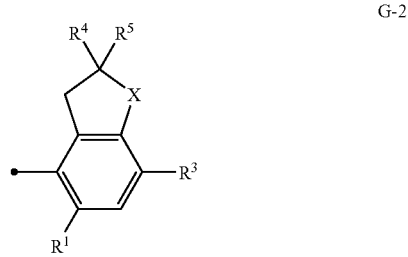

G-2

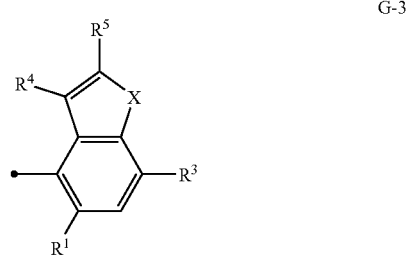

G-3

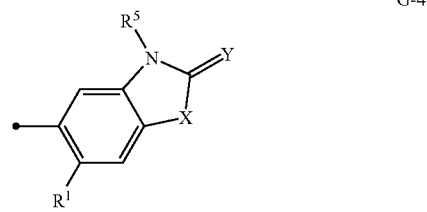

G-4

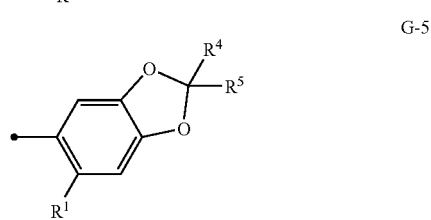

G-5

-continued

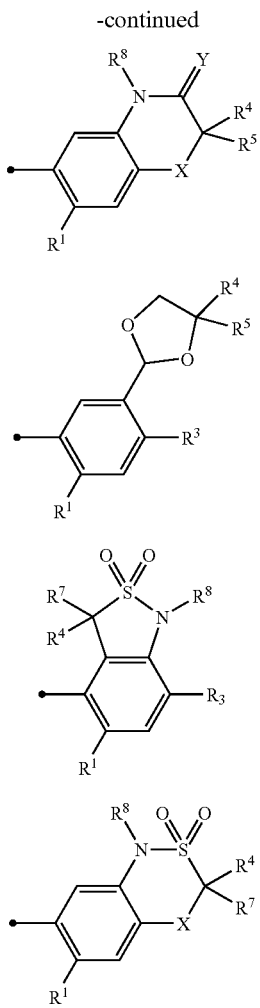

wherein in G-1 to G-9,

X represents an oxygen atom or sulfur atom;

Y represents an oxygen atom or sulfur atom;

$R^1$ represents a hydrogen atom or halogen atom;

$R^2$ represents a hydrogen atom, $C_1$-$C_8$ alkyl group, $C_1$-$C_8$ haloalkyl group, halogen atom, hydroxyl group, —$OR^9$ group, —SH group, —S(O)p$R^9$ group, —CO$R^9$ group, —CO$_2R^9$ group, —C(O)S$R^9$ group, —C(O)N$R^{11}R^{12}$ group, —CONH$_2$ group, —CHO group, —C$R^9$=NO$R^{18}$ group, —CH=C$R^{19}$CO$_2R^9$ group, —CH$_2$CH$R^{19}$CO$_2R^9$ group, —CO$_2$N=C$R^{13}R^{14}$ group, nitro group, cyano group, —NHSO$_2R^{15}$ group, —NHSO$_2$NH$R^{15}$ group, —N$R^9R^{20}$ group, —NH$_2$ group or phenyl group that may be substituted with one or more $C_1$-$C_4$ alkyl groups which may be the same or different:

p represents 0, 1 or 2;

$R^3$ represents $C_1$-$C_2$ alkyl group, $C_1$-$C_2$ haloalkyl group, —OCH$_3$ group, —SCH$_3$ group, —OCHF$_2$ group, halogen atom, cyano group, nitro group or $C_1$-$C_3$ alkoxy group substituted with a phenyl group which may be substituted on the ring with at least one substituent selected from a halogen atom, $C_1$-$C_3$ alkyl group, $C_1$-$C_3$ haloalkyl group, O$R^{28}$ group, N$R^{11}R^{28}$ group, S$R^{28}$ group, cyano group, CO$_2R^{28}$ group and nitro group;

$R^4$ represents a hydrogen atom, $C_1$-$C_3$ alkyl group or $C_1$-$C_3$ haloalkyl group;

$R^5$ represents a hydrogen atom, $C_1$-$C_3$ alkyl group, $C_1$-$C_3$ haloalkyl group, cyclopropyl group, vinyl group, $C_2$ alkynyl group, cyano group, —C(O)$R^{20}$ group, —CO$_2R^{20}$ group, —C(O)N$R^{20}R^{21}$ group, —CH$R^{16}R^{17}$CN group, —C$R^{16}R^{17}$C(O)$R^{20}$ group, —C$^{16}R^{17}$CO$_2R^{20}$ group, —C$R^{16}R^{17}$C(O)N$R^{20}R^{21}$ group, —CH$R^{16}$OH group, —CH$R^{16}$OC(O)$R^{20}$ group or —OCH$R^{16}$OC(O)N$R^{20}R^{21}$ group, or, when G represents G-2 or G-6, $R^4$ and $R^5$ may represent C=O group together with the carbon atom to which they are attached;

$R^6$ represents $C_1$-$C_6$ alkyl group, $C_1$-$C_6$ haloalkyl group, $C_2$-$C_6$ alkoxyalkyl group, $C_3$-$C_6$alkenyl group or $C_3$-$C_6$ alkynyl group;

$R^7$ represents a hydrogen atom, $C_1$-$C_6$ alkyl group, $C_1$-$C_6$ haloalkyl group, halogen atom, —S(O)$_2$($C_1$-$C_6$ alkyl) group or —C(=O)$R^{22}$ group;

$R^8$ represents a hydrogen atom. $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_3$-$C_8$ alkoxyalkoxyalkyl group, $C_3$-$C_8$ haloalkynyl group, $C_3$-$C_8$ haloalkenyl group, $C_1$-$C_8$ alkylsulfonyl group, $C_1$-$C_8$ haloalkylsulfonyl group, $C_3$-$C_8$ alkoxycarbonylalkyl group, —S(O)$_2$NH($C_1$-$C_8$alkyl) group, —C(O)$R^{23}$ group or benzyl group which may be substituted with $R^{24}$ on the phenyl ring;

$R^9$ represents $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_2$-$C_8$ alkylthioalkyl group, $C_2$-$C_8$ alkylsulfonylalkyl group, $C_2$-$C_8$ alkylsulfonylalkyl group, $C_4$-$C_8$ alkoxyalkoxyalkyl group, $C_4$-$C_8$ cycloalkylalkyl group, $C_4$-$C_8$ cycloalkoxyalkyl group, $C_4$-$C_8$ alkenyloxyalkyl group, $C_4$-$C_8$ alkynyloxyalkyl group, $C_3$-$C_8$ haloalkoxyalkyl group, $C_4$-$C_8$ haloalkenyloxyalkyl group, $C_4$-$C_8$ haloalkynyloxyalkyl group, $C_4$-$C_8$ cycloalkylthioalkyl group, $C_4$-$C_8$ alkenylthioalkyl group, $C_4$-$C_8$ alkynylthioalkyl group. $C_1$-$C_4$ alkyl group substituted with a phenoxy group which may be substituted on the ring with at least one substituent selected from a halogen atom, $C_1$-$C_3$ alkyl group and $C_1$-$C_3$ haloalkyl group, $C_1$-$C_4$ alkyl group substituted with a benzyloxy group which may be substituted on the ring with at least one substituent selected from a halogen atom, $C_1$-$C_3$ alkyl group and $C_1$-$C_3$ haloalkyl group, $C_4$-$C_8$ trialkylsilylalkyl group, $C_2$-$C_8$ cyanoalkyl group, $C_3$-$C_8$ halocycloalkyl group, $C_3$-$C_8$ haloalkenyl group, $C_5$-$C_8$ alkoxyalkenyl group, $C_5$-$C_8$ haloalkoxyalkenyl group, $C_5$-$C_8$ alkylthioalkenyl group, $C_3$-$C_8$ haloalkynyl group, $C_5$-$C_8$ alkoxyalkynyl group, $C_5$-$C_8$ haloalkoxyalkynyl group, $C_5$-$C_8$ alkylthioalkynyl group, $C_2$-$C_8$ alkylcarbonyl group, benzyl group which may be substituted on the ring with at least one substituent selected from a halogen atom, $C_1$-$C_3$alkyl group, $C_1$-$C_3$haloalkyl group, —O$R^{28}$ group —N$R^{11}R^{28}$ group, —S$R^{28}$ group, cyano group, —CO$_2R^{28}$ group and nitro group, —C$R^{16}R^{17}$CO$R^{10}$ group, —C$R^{16}R^{17}$CO$_2R^{20}$ group, —C$R^{16}R^{17}$P(O) (O$R^{10}$)$_2$ group, —C$R^{16}R^{17}$P(S) (O$R^{10}$)$_2$ group, —C$R^{16}R^{17}$C(O)N$R^{11}R^{12}$ group, —C$R^{16}R^{17}$C(O)NH$_2$ group, —C(=C$R^{26}R^{27}$)CO$R^{10}$ group, —C(=C$R^{26}R^{27}$) CO$_2R^{20}$ group, —C(=C$R^{26}R^{27}$)P(O)(O$R^{10}$)$_2$ group, —C(=C$R^{26}R^{27}$)P(S)(O$R^{10}$)$_2$ group, —C(=C$R^{26}R^{27}$)C(O)N$R^{11}R^{12}$ group, —C(=C$R^{26}R^{27}$)C(O)NH$_2$ group, or any one of rings shown in Q-1 to Q-7:

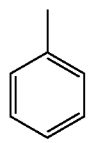

Q-1

Q-2 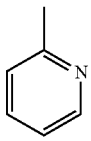

Q-3 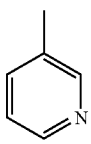

Q-4 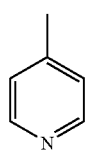

Q-5 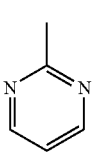

Q-6 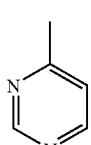

Q-7 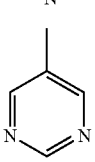

which may be substituted on the ring with at least one substituent selected from a halogen atom, $C_1$-$C_6$ alkyl group, $C_1$-$C_6$ haloalkyl group, $C_2$-$C_6$ alkenyl group, $C_2$-$C_6$ haloalkenyl group, $C_2$-$C_6$ alkynyl group, $C_3$-$C_6$ haloalkynyl group, $C_2$-$C_6$ alkoxyalkyl group, —$OR^{28}$ group, —$SR^{28}$ group, —$NR^{11}R^{28}$ group, $C_3$-$C_8$ alkoxycarbonylalkyl group, $C_2$-$C_4$ carboxyalkyl group, —$CO_2R^{28}$ group and cyano group;

$R^{10}$ represents a $C_1$-$C_6$ alkyl group, $C_2$-$C_6$ alkenyl group, $C_3$-$C_6$ alkynyl group or tetrahydrofuranyl group;

$R^{11}$ and $R^{13}$ independently represent a hydrogen atom or $C_1$-$C_4$ alkyl group;

$R^{12}$ represents $C_1$-$C_6$ alkyl group, $C_3$-$C_6$ cycloalkyl group, $C_3$-$C_6$ alkenyl group, $C_3$-$C_6$ alkynyl group, $C_2$-$C_6$ alkoxyalkyl group, $C_1$-$C_6$ haloalkyl group, $C_3$-$C_6$ haloalkenyl group, $C_3$-$C_6$ haloalkynyl group, phenyl group which may be substituted on the ring with at least one substituent selected from a halogen atom, $C_1$-$C_4$ alkyl group and $C_1$-$C_4$ alkoxy group or —$CR^{16}R^{17}CO_2R^{25}$ group; or, $R^{11}$ and $R^{12}$ together may represent —$(CH_2)_5$—, —$(CH_2)_4$— or —$CH_2CH_2OCH_2CH_2$—, or in that case the resulting ring may be substituted with a substituent selected from a $C_1$-$C_3$ alkyl group, a phenyl group and benzyl group;

$R^{14}$ represents a $C_1$-$C_4$ alkyl group or phenyl group which may be substituted on the ring with a substituent selected from a halogen atom, $C_1$-$C_3$ alkyl group and $C_1$-$C_3$ haloalkyl group; or, $R^{13}$ and $R^{14}$ may represent $C_3$-$C_8$ cycloalkyl group together with the carbon atom to which they are attached;

$R^{15}$ represents $C_1$-$C_4$ alkyl group, $C_1$-$C_4$ haloalkyl group or $C_3$-$C_6$ alkenyl group;

$R^{16}$ and $R^{17}$ independently represent a hydrogen atom or $C_1$-$C_4$ alkyl group, $C_1$-$C_4$ haloalkyl group, $C_2$-$C_4$ alkenyl group, $C_2$-$C_4$ haloalkenyl group, $C_2$-$C_4$ alkynyl group, $C_3$-$C_4$ haloalkynyl group; or, $R^{16}$ and $R^{17}$ may represent $C_3$-$C_6$ cycloalkyl group with the carbon atom to which they are attached, or the ring thus formed may be substituted with at least one substituent selected from a halogen atom, a $C_1$-$C_3$ alkyl group and $C_1$-$C_3$ haloalkyl group;

$R^{18}$ represents a hydrogen atom, $C_1$-$C_6$ alkyl group, $C_3$-$C_6$ alkenyl group or $C_3$-$C_6$ alkynyl group;

$R^{19}$ represents a hydrogen atom, $C_1$-$C_4$ alkyl group or halogen atom, $R^{20}$ represents a hydrogen atom, $C_1$-$C_6$ alkyl group, $C_3$-$C_6$ cycloalkyl group, $C_3$-$C_6$ alkenyl group, $C_3$-$C_6$ alkynyl group, $C_2$-$C_6$ alkoxyalkyl group, $C_1$-$C_6$ haloalkyl group, $C_3$-$C_6$ haloalkenyl group, $C_3$-$C_6$ haloalkynyl group, phenyl group which may be substituted on the ring with at least one substituent selected from a halogen atom, $C_1$-$C_4$ alkyl group and —$OR^{28}$ group, or —$CR^{16}R^{17}CO_2R^{25}$ group;

$R^{21}$ represents a hydrogen atom, $C_1$-$C_2$ alkyl group or —$CO_2(C_1$-$C_4$ alkyl) group;

$R^{22}$ represents a hydrogen atom, $C_1$-$C_6$ alkyl group, $C_1$-$C_6$ alkoxy group or $NH(C_1$-$C_6$ alkyl) group;

$R^{23}$ represents $C_1$-$C_6$ alkyl group, $C_1$-$C_6$ haloalkyl group, $C_1$-$C_6$ alkoxy group, $NH(C_1$-$C_6$ alkyl) group, benzyl group, $C_2$-$C_8$ dialkylamino group or phenyl group which may be substituted with $R^{24}$;

$R^{24}$ represents $C_1$-$C_6$ alkyl group, 1 to 2 halogen atoms, $C_1$-$C_6$ alkoxy group or $CF_3$ group:

$R^{25}$ represents $C_1$-$C_6$ alkyl group, $C_1$-$C_6$ haloalkyl group, $C_3$-$C_6$ alkenyl group, $C_3$-$C_6$ haloalkenyl group, $C_3$-$C_6$ alkynyl group or $C_3$-$C_6$ haloalkynyl group;

$R^{26}$ and $R^{27}$ each represent independently a hydrogen atom, $C_1$-$C_4$ alkyl group, $C_1$-$C_4$ haloalkyl group, $C_2$-$C_4$ alkenyl group, $C_2$-$C_4$ haloalkenyl group, $C_2$-$C_4$ alkynyl group, $C_3$-$C_4$ haloalkynyl group, —$OR^{28}$ group, —$NHR^{28}$ group, or —$SR^{28}$ group; or, $R^{26}$ and $R^{27}$ may represent $C_3$-$C_8$ cycloalkyl group with the carbon atom to which they are attached, or each of the ring thus formed may be substituted with at least one substituent selected from a halogen atom, $C_1$-$C_3$ alkyl group and $C_1$-$C_3$ haloalkyl group; and, $R^{28}$ represents a hydrogen atom, $C_1$-$C_6$ alkyl group, $C_1$-$C_6$ haloalkyl group, $C_3$-$C_6$ alkenyl group, $C_3$-$C_6$ haloalkenyl group, $C_3$-$C_6$ alkynyl group, $C_3$-$C_6$ haloalkynyl group, $C_2$-$C_4$ carboxyalkyl group, $C_3$-$C_8$ alkoxycarbonylalkyl group, $C_3$-$C_8$ haloalkoxycarbonylalkyl group, $C_5$-$C_9$ alkenyloxycabonylalkyl group, $C_5$-$C_9$ haloalkenyloxycabonylalkyl group, $C_5$-$C_9$ alkynyloxycabonylalkyl group, $C_5$-$C_9$ haloalkynyloxycabonylalkyl group, $C_5$-$C_9$ cycloalkoxycabonylalkyl group or $C_5$-$C_9$ halocycloalkoxycabonylalkyl group.

And further, there may be, specifically for example, a compound having the following formula (hereinafter, may be referred to as the compound (II)):

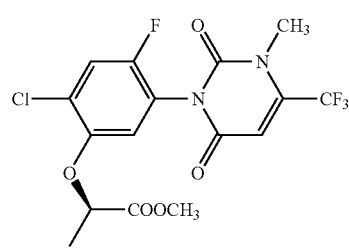

butafenacil, flufenpyr-ethyl,
methyl 2-[2-chloro-5-[3,6-dihydro-3-methyl-2,6-dioxo-4-(trifluoromethyl)-1(2H)-pyrimidinyl-4-fluorophenoxy] phenoxyacetate,
ethyl [3-[2-chloro-5-[3,6-dihydro-3-methyl-2,6-dioxo-4-(trifluoromethyl)-1(2H)-2-pyrimizinyl]-4-fluorophenoxy]-2-pyridazinyl]oxyacetate,
2-[4-chloro-2-fluoro-5-(2-propynyloxy)phenyl]-4-methy -5-(trifluoromethyl)-3(2H)-pyridazinone,
carfentrazone-ethyl, sulfentrazone and the like.

In the method for controlling weeds of the present invention, the compound to be applied to a cultivation area of the present plant Is a protoporphyrinogen IX oxidase inhibitory-type herbicidal compound and selected from the group consisting of:
(1) flufenpyr-ethyl,
(2) 2-[4-chloro-2-fluoro-5-(2-propynyloxy)phenyl]-4-methy-5-(trifluoromethyl)-3(2H)-pyridazinone,
(3) carfentrazone-ethyl, and
(4) sulfentrazone.

Here, "flufenpyr-ethyl" is the compound of CAS registry no. 188489-07-8, "carfentrazone-ethyl" is the compound of CAS registry no. 128639-02-1, "sulfentrazone" is the compound of CAS registry no. 122836-35-5. Hereinafter, 2-(4-chloro-2-fluoro-5-(2-propynyloxy)phenyl]-4-methy-5-(trifluoromethyl)-3(2H)-pyridazinone (CAS registry no. 188489-06-7) may be referred to as the compound (I).

When said herbicidal compounds are applied to the cultivation area of the present plant, insecticidal compounds, fungicidal compounds, plant growth regulatory compounds, fertilizer ingredients and the like may also be applied as needed along with said herbicidal compound.

In the present invention, sequence homology refers to the homology between two nucleotide sequences or two amino acid sequences. Such "sequence homology" may be determined by comparing the two sequences, each aligned in an optimal state, over the whole region of the test sequences. As such, additions or deletions (for example, gaps) can be utilized in the optimal alignment of the test nucleic acid sequences or amino acid sequences. Such sequence homology can be calculated through the step of producing the alignment conducted by a homology analysis using a program such as FASTA (Pearson & Lipman, Proc. Natl. Acad. Sci. USA, 4, 2444-2448 (1988)), BLAST (Altschul et al., Journal of Molecular Biology, 215, 403-410 (1990)), CLUSTAL W (Thompson, Higgins & Gibson, Nucleic Acid Research, 22, 4673-4680 (1994a)) and the like. Such programs, for example, can be typically utilized on the webpage (www.ddbj.nig.ac.jp) of the DNA Data Bank of Japan (the international databank operated within the Center for Information Biology and DNA Data Bank of Japan). Further, the sequence homology may be determined by utilizing a commercially available sequence analysis software. Specifically for example, it can be calculated by producing an alignment conducted by a homology analysis by the Lipman-Pearson method (Lipman, D. J. and Pearson, W. R., Science, 227, 1435-1441, (1985)) utilizing GENETYX-WIN Ver. 6 (manufactured by GENETYX Corporation). For example, as the results of alignment at homology analysis of the amino acid sequence of SEQ ID NO: 1 and the amino acid sequence of SEQ ID NO: 2 by using the method, it is calculated 90% of sequence homology.

Cytochrome P450 used in the present invention is a family of proteins containing protoheme and named for its spectroscopic property indicating Soret near 450 nm when it binds with carbon monoxide at a reduction state. The cytochrome P450 exists in various animal tissues, plant tissues, fungi, yeast and bacteria. The cytochrome p450 has abilities to catalyze, with free oxygen and 2 electrons generally derived from NADPH, or rarely derived from NADH, monooxygenation of the present herbicidal compounds and the like and subsequent elimination of functional groups. The cytochrome p450 may be (1) a type to be provided electron from the electron transfer system with both of ferredoxin and NADPH-ferredoxin reductase, or (2) a type to be provided electron directly from NADPH-cytochrome P450 reductase. Preferably, it may be the former. The cytochrome P450 in the former may be located in any one of subcellular organelles of a host cell or in the cytoplasm. The ferredoxin may be an endogenous ferredoxin in the host cell or a foreign ferredoxin produced in the host cell wherein a foreign ferredoxin gene has been introduced into the host cell.

Preferable cytochrome P450 used in the present invention may be cytochrome P450 derived from *actinomyces*. Here, *actinomyces* is a family of prokaryote belonging to the Actinomycetales, which are a family of Gram-positive bacteria to be grouped 8 genera of *Streptomyces, Actinomyces, Mycobacterium, Frankia, Nocardia* and the like. More preferable cytochrome P450 may be cytochrome P450 derived from *actinomyces* belonging to *Streptomyces*, concretely, for example, cytochrome P450 derived from *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus. Streptomyces lanatus, Streptomyces misawanensis, Streptomyces pallidus, Streptomyces roseorubens, Streptomyces rutgersensis, Streptomyces steffisburgensis, Saccharopolyspora taberi* and the like. Concrete examples of cytochrome P450 derived from *actinomyces* beonging to *Streptomyces* may be cytochrome P450 having the amino acid sequence of SEQ ID NO: 1, cytochrome P450 having the amino acid sequence of SEQ ID NO: 2, cytochrome P450 having an amino acid sequence having 90% or more sequence homology with the amino acid sequence of SEQ ID NO: 1 or 2, and the like.

The gene-(DNA) having a nucleotide sequence encoding an amino acid sequence of cytochrome P450 may be a cytochrome P450 gene having naturally-occurring nucleotide sequence, and a gene having a nucleotide sequence encoding cytochrome P450 in which the codon usage has been optimized for its expression in the host cell. Also, it may be a gene encoding a protein having cytochrome P450 activity wherein substitution, addition, deletion or the like of amino acid has been introduced to an amino acid sequence of a naturally-occurring cytochrome P450, and, a gene encoding a protein selected based on the cytochrome P450 activity. Concretely, the gene encoding cytochrome P450 may be a gene encoding cytochrome P450 described in International Patent Publication WO 03040370.

The gene having a nucleotide sequence encoding an amino acid sequence of the cytochrome P450 introduced to the host cell may be located in any one of subcellular organelles in the cell or in chromosome in nuclear. Also, the cytochrome P450 may be located in any one of subcellular organelles, cytoplasm or extracellular space, preferably subcellular organelles, more preferably plastid.

For the transition of cytochrome P450 to subcellular organelles in the cell, it may be introduced to the host cell a chimeric DNA in which a DNA having a nucleotide sequence encoding organelles transit peptide sequence is linked in frame upstream of a DNA having a nucleotide sequence encoding an amino acid sequence of cytochrome P450. Here, "linked in frame" means that the reading frame of the nucleotide sequence encoding the organelles transit peptide sequence and the reading frame of the nucleotide sequence encoding the amino acid sequence of the cytochrome P450 are linked to form one continuous reading frame. The transit peptide sequence to transit and localize the protein to subcellular organelles in the host cell is, for example, a transit peptide sequence of a cytoplasmic precursor of a chloroplast protein of a plant described in U.S. Pat. No. 5,717,084, and a chimeric sequence comprising plural kinds of transit peptide sequences described in U.S. Pat. No. RE 36,449 etc. Concretely, it is, for example, chloroplast transit peptide sequence derived from ribulose-1,5-bisphosphate carboxylase (hereinafter, may be referred to as RuBPCO) small subunit of soybean which is obtainable by a method described in International Patent Publication WO03040370.

As the method of artificially causing deletions, additions or substitutions of amino acid residues in an amino acid sequence of the cytochrome P450 described above, for example, there is a method comprising a steps of carrying out site-directed mutagenesis on a DNA having a nucleotide sequence encoding the amino acid sequence, and then allowing the expression of such DNA by a conventional method. Concretely, for example, it may be a method utilizes amber mutations (gapped duplex method, Nucleic Acids Res., 12, 9441-9456 (1984)), a method by PCR utilizing primers for introducing a mutation and the like. Also, for example, it may be a method comprising the steps of carrying out random mutagenesis on a DNA having a nucleotide sequence encoding the amino acid sequence and the like. Concretely, for example, it may be a method of conducting PCR by utilizing the DNA having a nucleotide sequence encoding the amino acid sequence as a template and a primer pair which can amplify the full length of the DNA, under the conditions in which concentration of each of DATP, dTTP, dGTP and dCTP utilized as a substrate are changed, or, under the conditions in which the concentration of $Mg^{2+}$ is made increase more to promote the polymerase reaction, and the like. Such methods of PCR may be, for example, the conventional methods described in Method in Molecular Biology, (31), 1994, 97-112 and the like.

In the method for confirming cytochrome P450 activity of the protein to which mutation has been introduced as described above, for example, the DNA having a nucleotide sequence encoding the amino acid sequence of the protein to which the mutation has been introduced is inserted to a vector plasmid firstly. The vector plasmid is introduced in a host cell to express the DNA, as described in WO03040370 and the like. Thus, such activity may be confirmed by adding and reacting the present herbicidal compound as a substrate, ferredoxin and NADPH-ferredoxin reductase to an extract of the host cell in which mutated cytochrome P450 was produced, and measuring the decreased substrate in the reaction mixture after the reaction.

The DNA having a nucleotide sequence encoding an amino acid sequence wherein substitution, addition, deletion or the like of amino acid has been introduced to the particular amino acid sequence of cytochrome P450 can be obtained from various DNA libraries, by utilizing a polynucleotide having a nucleotide sequence complementary to the nucleotide sequence encoding the particular amino acid sequences described above as a probe and carrying out hybridization under stringent conditions according to the conventional genetic engineering methods. Also, the DNA having a nucleotide sequence encoding an amino acid sequence having 90% or more sequence homology to the particular amino acid sequences, concretely, for example, a DNA having a nucleotide sequence encoding cytochrome P450 having an amino acid sequence having 90% or more sequence homology to the amino acid sequence of SEQ ID NO: 1 or 2 can be obtained from various DNA libraries, by utilizing a polynucleotide having a nucleotide sequence complementary to the nucleotide sequence encoding the particular amino acid sequence as a probe and carrying out hybridization under stringent conditions according to the conventional genetic engineering methods. As the "stringent conditions", there can be mentioned, for example, the conditions under which hybridization is performed at 68° C. in a solution containing 6×SSC (let the solution containing 3 M NaCl and 0.3 M trisodium citrate be 20×SSC) and then the hybridized membrane is washed at 68° C. with 0.1×SSC and 0.5% SDS in a hybridization conducted according to the conventional method described in such as Sambrook, J., Frisch, E. F., and Maniatis, T.; chapter 9.53, Molecular Cloning 2nd edition, Cold Spring Harbor Press (1989). The salt concentration in the washing step can be selected, for example, from the conditions of 2×SSC (low stringency condition) to the conditions of 0.1×SSC (high stringency condition). A temperature in the washing step can be selected, for example, from room temperature (low stringency condition) to 68° C. (high stringency condition). Alternatively, both of the salt concentration and temperature may be changed.

To introduce to plant and express the gene to be introduced in the present invention, generally, a DNA having a nucleotide sequence encoding the amino acid sequence of the protein to be expressed, a DNA in which aforementioned DNA and a promoter functional in the plant cell is operably linked or the like, may be inserted to a vector plasmid functional in the plant cell, and introduced to the plant cell. When the vector plasmid already possessing the promoter functional in the plant cell is utilized, aforementioned DNA may be inserted downstream of the promoter present in the vector plasmid so that the promoter and the DNA having a nucleotide sequence encoding the amino acid sequence of the protein to be expressed are operably linked.

Here, the promoter functional in the host cell such as plant cell is a nucleotide sequence which is connected 5' upstream of a nucleotide sequence of a gene having a nucleotide sequence encoding an amino acid sequence of a protein (the structural gene) and has a function to control initiation of the transcription of the gene in the host cell such as plant cell. As the functional promoter in the plant cell, for example, there is mentioned T-DNA derived constitutive promoters such as nopaline synthase gene promoter and octopine synthase gene promoter; plant virus-derived promoters such as cauliflower mosaic virus derived 19S and 35S promoters; inducible promoters such as phenylalanine ammonia-lyase gene promoter, chalcone synthase gene promoter and pathogenesis-related protein gene promoter; the plant promoter described in International Patent Publication WO2000020613, and the like. Also, a terminator functional in the host cell such as plant cell may be linked downstream of a DNA in which the promoter functional in the host cell such as plant cell described above and a DNA having a nucleotide sequence encoding an amino acid sequence of the protein showing PPO activity or the cytochrome P450 are operably linked.

The terminator functional in the host cell such as plant cell is a nucleotide sequence which is connected 3' downstream of a nucleotide sequence of a gene having a nucleotide sequence encoding an amino acid sequence of a protein (the structural gene) and has a function to add polyadenine sequence for stabilization of the transcription of the gene. As the functional terminator in the plant cell, for example, there is mentioned T-DNA derived constitutive terminators such as nopaline synthase gene (NOS) terminator; plant virus derived terminators such as terminators of garlic virus GV1 or GV2; the plant terminator described in International Patent Publication WO2000020613; and the like.

As the plant cell to be utilized as the host cell, there are, for example, plant cells derived from dicotyledonous plant, including solanaceous plant such as eggplant, potato and tomato; cruciferous plant such as rape, canola, lettuce, sugar beet and *arabidopsis*; leguminous plant such as soybean, pea and alfalfa; rosaceous plant such as apple, pear and almond; citrus such as orange and lemon; cotton, *linum*, sunflower, banana, grape, almond, poplar, and plant cells derived from monocotyledonous plant including poaceous plant such as corn, rice, wheat, barley, rye, oat and sorghum and the like.

As the plant cell to be utilized as the host cell, there are various plant cells such as plant tissues, plant bodies, cultured cells, seeds and the like.

As the method for introducing into a host cell such as a plant cell DNA having the structural gene to which a promoter and a terminator functional in the host cell such as the plant cell are linked, there are, for example, a method by infection with *agrobacterium* (Japanese examined patent publication No. Hei2-58917 and Japanese unexamined patent publication No. Syo-70080), electroporation into protoplast (Japanese unexamined patent publication No. Syo-60-251887 and Japanese unexamined patent publication No. Hei5-68575), particle gun methods (Japanese unexamined patent publication No. Hei 5-508316 and Japanese unexamined patent publication No. Syo-63-258525) or the like.

In such case, the transformant to which the DNA has been introduced can be selected based on phenotype of a selective marker gene, by simultaneously introducing a selective marker gene selected from hygromycin phosphotransferase gene, neomycin phosphotransferase gene, chloramphenicol acetyltransferase gene and the like, and a DNA having a nucleotide sequence encoding an amino acid sequence of the cytochrome P450 showing the protoporphyrinogen IX oxidase inhibitory-type herbicidal compound metabolizing activity. The selective marker gene and the DNA having a nucleotide sequence encoding an amino acid sequence of the cytochrome P450 showing the protoporphyrinogen IX oxidase inhibitory-type herbicidal compound metabolizing activity may be tandemly inserted into the same vector and introduced. A vector plasmid comprising the selective marker gene and the DNA having a nucleotide sequence encoding an amino acid sequence of the cytochrome P450 showing the protoporphyrinogen IX oxidase inhibitory-type herbicidal compound metabolizing activity (the present DNA) may be introduced simultaneously. A transformant to which the objective gene has been introduced may also be selected by culturing with a medium containing the protoporphyrinogen IX oxidase inhibitory-type herbicidal compound, plant cells to which a vector comprising the objective gene has been introduced and isolating grown clones.

The presence of the present DNA in the transformant may be confirmed by preparing DNA from the transformant and then conducting with the prepared DNA genetic engineering analysis methods (such as confirming restriction enzyme sites, analysis of nucleotide sequence, southern hybridization, PCR and the like) described in, for example, "Molecular Cloning: A Laboratory Manual $2^{nd}$ edition" (1989), Cold Spring Harbor Laboratory Press and the like.

Specifically, for example, rice or *Arabidopsis* having introduced therein the present DNA can be obtained according to the method described in Model-Shokubutu-No-Jikken-Protocol: Ine, Shiroinunazuna-Hen (Supervisors: Koh SHIMAMOTO and Kiyotaka OKADA, Shujun-sha, 1996), Fourth chapter. Further, there can be obtained a soybean having introduced therein the present DNA by an introduction into a soybean somatic embryo with a particle gun according to the method described in Japanese Unexamined Patent Publication No. 3-291501. Likewise, a maize having introduced therein the present DNA can be obtained by an introduction into maize somatic embryo with a particle gun according to the method described by Fromm, M. E., et al., Bio/Technology, 8; p 838 (1990). Wheat having introduced therein the present DNA can be obtained by introducing the DNA into aseptically-cultured immature embryo with a particle gun according to a conventional method described by TAKUMI et al., Journal of Breeding Society (1995), 44: Extra Vol. 1, p 57. Likewise, barley having introduced therein the present DNA can be obtained by an introduction into aseptically-cultured barley immature embryo with a particle gun according to a conventional method described by HAGIO, et al., Journal of Breeding Society (1995), 44; Extra Vol. 1, p 67.

From thus produced transformant, a transgenic plant to which the present DNA have been introduced can be obtained, by regenerating a plant body according to the method for culturing the plant cell described in, for example, "Shokubutu-Saibou-Soshiki-Baiyo, Jissai, Ouyou, Tenbou", Harada, Komamine Ed., Rikogakusha (1979), p65-118 and the like.

Further, by crossing of the transgenic plant having introduced and expressed therein the present DNA and a plant of the targeted variety, the present DNA can be introduced to a chromosome of the plant of the targeted variety, and the plant of the targeted variety to which the present DNA has been introduced can be obtained.

Specifically, for example, to produce a recombinant soybean line to which a DNA having a nucleotide sequence encoding the amino acid sequence of SEQ ID NO: 1 has been introduced, the DNA is introduced to somatic embryos of soybean by using a particle gun according to the method described in Japanese unexamined patent publication No. Hei3-291501. Next, for investigating the resistance of the obtained recombinant soybean line to the present herbicidal compound, it may be carried out scoring evaluation as to sensitivity in a spray test of the present herbicidal compound according to the method described below in Example 5 and the like (evaluation by scoring index based on the degree of phytotoxicity as dying of the individual and browning or whitening of the leaves or stems caused by compound spraying).

Also, concretely, for example, to produce a recombinant corn line to which a DNA having a nucleotide sequence encoding the amino acid sequence of SEQ ID NO: 1 has been introduced, the DNA is introduced to somatic embryos of corn by using a particle gun according to the method described in Fromm, M. E., et al., Bio/Technology, 8; p838 (1990). Next, for investigating the resistance of the obtained recombinant corn line to the present herbicidal compound, it may be carried out scoring evaluation as to sensitivity in a spray test of the present herbicidal compound according to the method described below in Example 5 and the like (evaluation by scoring index based on the degree of phytotoxicity as dying of the individual and browning or whitening of the leaves or stems caused by compound spraying).

Also, concretely, for example, to produce a recombinant cotton line to which a DNA having a nucleotide sequence encoding the amino acid sequence of SEQ ID NO: 1 has been introduced, the DNA is introduced to cotton according to *Agrobacterium* infection method. Next, for investigating the resistance of the obtained recombinant cotton line to the present herbicidal compound, it may be carried out scoring evaluation as to sensitivity in a spray test of the present herbicidal compound according to the method described below in Example 5 and the like (evaluation by scoring index based on the degree of phytotoxicity as dying of the individual and browning or whitening of the leaves or stems caused by compound spraying).

Also, concretely, for example, to produce a recombinant rape line to which a DNA having a nucleotide sequence encoding the amino acid sequence of SEQ ID NO: 1 has been introduced, the DNA is introduced to rape according to *Agrobacterium* infection method. Next, for investigating the resistance of the obtained recombinant rape line to the present herbicidal compound, it may be carried out scoring evaluation as to sensitivity in a spray test of the present herbicidal compound according to the method described below in Example 5 and the like (evaluation by scoring index based on the degree of phytotoxicity as dying of the individual and browning or whitening of the leaves or stems caused by compound spraying).

Also, concretely, for example, to produce a recombinant wheat line to which a DNA having a nucleotide sequence encoding the amino acid sequence of SEQ ID NO: 1 has been introduced, the DNA is introduced to calli derived from immature embryo of wheat by using a particle gun according to the method described in TAKUMI et al., Journal of Breeding Society (1995), 44: Extra Vol. 1, p 57. Next, for investigating the resistance of the obtained recombinant wheat line to the present herbicidal compound, it may be carried out scoring evaluation as to sensitivity in a spray test of the present herbicidal compound according to the method described below in Example 5 and the like (evaluation by scoring index based on the degree of phytotoxicity as dying of the individual and browning or whitening of the leaves or stems caused by compound spraying).

In the method for controlling weeds of the present invention, an effective amount of the present herbicidal compound is applied to the cultivation area of the present plant. The amount of the application of the present herbicidal compound may be appropriately decided according to season of the application, variety of the weed, kind of the present herbicidal compound and the like.

Because degree of phytotoxicity of the present plant is highly reduced in applying the present herbicidal compound, the present plant can be grown well when the present herbicidal compound is sprayed or added to the area growing or culturing the present plant. By cultivating the present plant and applying a weed controlling agent containing the present herbicidal compound as an active ingredient to the cultivation area of the plant, it can be to remove efficiently plants such as weeds except for the present plant, then to improve the yield and quality of the present plant, to reduce the amount of application of weed controlling agents, to save the labor and the like. Thus the present invention may provide a method for controlling weeds which can increase options for herbicidal compounds to be selected according to the property of the target plant.

EXAMPLES

Hereinafter, the present invention is further explained with Examples in detail, but not limited thereto.

Example 1

Figure 2:
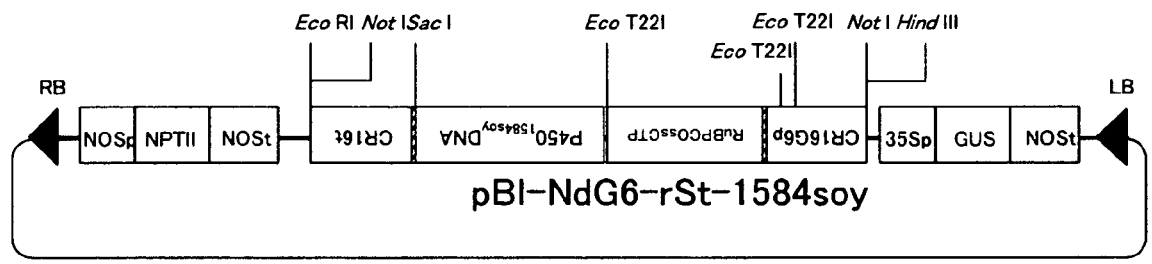
FIG. 2 shows the restriction map of the plasmid pBI-NdG6-rSt-1584soy.

Production of Recombinant Tobacco Plants into Which a Cytochrome P450 Gene has been Introduced Plasmid pBI-NdG6-rSt-1609soy (FIG. 1) (described in International Patent Publication WO0304370) is a binary vector plasmid to express the chimeric protein comprising the chloroplast transit peptide sequence of soybean (cv. Jack) RuBPCO small subunit and cytochrome P450 having the amino acid sequence of SEQ ID NO: 1 under the control of CR16G6 promoter (described in International Patent Publication WO00020613). Plasmid pBI-NdG6-rSt-1584 (FIG. 2) (described in International Patent Publication WO0304370) is a binary vector plasmid to express the chimeric protein comprising the chloroplast transit peptide sequence of soybean (cv. Jack) RuBPCO small subunit and cytochrome P450 having the amino acid sequence of SEQ ID NO: 2 under the control of CR16G6 promoter (described in International Patent Publication WO00020613).

These plasmids pBI-NdG6-rSt-1609soy and pBI-NdG6-rSt-1584soy were introduced separately to *Agrobacterium tumefaciens* LBA4404 strain (manufactured by Clontech). The resultant transformants were cultured on LB agar medium (0.5% Yeast extract, 1.0% Bacto tryptone, 0.5% NaCl) containing 300 µg/L streptomycin, 100µ/L rifampicin and 25µ/L kanamycin, followed by selection of drug resistant colonies to isolate a recombinant *Agrobacterium* strain having plasmid pBI-NdG6-rSt-1609soy and a recombinant *Agrobacterium* strain having plasmid pBI-NdG6-rSt-1584soy respectively.

Then, according to the method described in Manual for Gene Manipulation of Plant (by Hirofumi Uchimiya, Kodansha Scientific (1992)), gene introduction to tobacco was carried out. The above recombinant *Agrobacterium* strains were each cultured at 28° C. overnight in LB liquid medium containing 300 µg/L streptomycin, 100 µL/L rifampicin and 25µ/L kanamycin. To the obtained liquid culture medium, leaf disks sampled from aseptically-cultured tobacco (*Nicotinia tabacum* strain SR-1) were dipped. The leaf disks were planted on MS agar medium (MS inorganic salts, MS vitamins, 3% sucrose, and 0.8% agar; Murashige T. and Skoog F., Physiol. Plant. (1962) 15, p473) containing 0.1 mg/L naphthalene acetic acid and 1.0 mg/L benzyl aminopurine, and cultured in the light at room temperature for 2 days. Then, the leaf disks were washed with sterilized water, and cultured for 7 days on MS agar medium containing 0.1 mg/L naphthalene acetic acid, 1.0 mg/L benzyl aminopurine and 500 mg/L cefotaxime. Next, the leaf disks were transplanted to and cultured on MS agar medium containing 0.1 mg/L naphthalene acetic acid, 1.0 mg/L benzylaminopurine, 500 mg/L cefotaxime and 100 mg/L kandmycin. The culture was conducted continuously for 2 months while transplanting the leaf disks to fresh medium of the same composition at intervals of 2 weeks. During that time, the adventitious buds developed from the leaf disks were transplanted to and rooted on MS agar medium containing 100 mg/L kanamycin to obtain regenerated plants. Then, the regenerated plants were transplanted to and cultured on MS agar medium containing 100 mg/L kanamycin dispensed to culture pots (Technopot manufactured by SUMITOMO BAKELITE Co., Ltd) to obtain a recombinant tobacco individual into which the T-DNA region of plasmid pBI-NdG6-rSt-1609soy has been introduced and a recombinant tobacco individual into which the T-DNA region of plasmid pBI-NdG6-rSt-1584soy has been introduced. The obtained individuals were transplanted to growing pots containing horicultural soil (Kureha Engei Baido manufactured by Kureha Chemical Industry Co., Ltd.) from the culture pots, acclimated to the external environment in a growth chamber, then grown in a greenhouse. Flowers were covered with paper bags during flowering period to avoid crossing with other individuals, and seeds were harvested from them.

Example 2

Selection of the Recombinant Tobacco Individual with an Accumulation of the Cytochrome P450

From the recombinant tobacco individuals obtained in Example 1, recombinant tobacco individuals in which the protein having the amino acid sequence of SEQ ID NO: 1 or 2 has been accumulated in their leaves were selected by using Western blotting method. Firstly, about 1 cm square of a leaf piece of the recombinant tobacco to be assayed was sampled, and put into 2 mL sampling tube. It was added one zirconia bead of 5 mm diameter (YTZ ball manufactured by NIKKATO CORPORATION) therein and put the lid thereon, and then quickly frozen in liquid nitrogen. Using a cell disruption apparatus (Mixer Mill MM300 manufactured by QIAGEN), it was shaken twice at the rate of 30 times/second for 15 seconds to homogenize the sample. By adding 0.1 mL of sample buffer (PBS buffer (137 mM sodium chloride, 8.1 mM disodium hydrogenphosphate, 2.68 mM potassium chloride, and 1.47 mM potassium dihydrogenphosphate) containing 1 mM phenylmethylsulfonyl fluoride) and shaking, proteins were extracted. Sampling one part of the extract, the concentration of the protein in the extract was measured by using BIO-RAD Protein Assay Kit (manufactured by BIO-RAD) and measuring absorbance at 595 nm according to the protocol attached the kit using bovine serum albumin as a standard. To the extract thus prepared from the recombinant tobacco individual, it was mixed the same volume of 2×SDS sample buffer (manufactured by Nakalai tesque), heated 100° C. for 3 minutes, and then cooled on ice. It was added into the well of SDS-PAGE gel (PAG mini "Daiich" manufactured by Daiichi Pure Chemicals Co., Ltd) such that 10 μg protein was applied per 1 well. Electrophoresis was carried out in the SDS-PAGE electrophoresis buffer (tris(hydroxymethyl)aminomethane 15 g, glycine 72 g, and SDS 5 g/L) at 40 mA per gel for 1 hour. From this gel, the proteins after the electrophoresis were transferred onto PVDF membrane (Immobilon-P manufactured by Millipore) for 30 minutes at 10 V in transfer buffer of Bjerrum and Schafer-Nielsen (48 mM tris (hydroxymethyl)amino methane, 39 mM glycine, and 20% methanol) by using a semi-dry blotting device (Transblot SD cell manufactured by BIO-RAD) according to the attached instruction manual. The membrane was treated by using Immune blot kit (manufactured by BIO-RAD) and anti-rabbit IgG antibody labeled with alkaline phosphatase, and then the coloring reaction was carried out by using NBT/BCIP coloring system to detect a band of the protein extracted from the leaf of the recombinant tobacco individual. Firstly, the blocking treatment was carried out by shaking the membrane gently in TBS buffer (20 mM Tris-HCl (pH7.5) and 0.5 mM sodium chloride) containing 3% gelatin for 30 minutes at room temperature. Then, the membrane was washed with TBS buffer for 5 minutes, and gently shaken for 1 hour at room temperature with antiserum of the primary antibody diluted 3,000 fold with TBS buffer containing 0.05% Tween 20 to carry out the primary antibody reaction. As the primary antibody, the rabbit antiserum was used which was obtained by immunization of rabbit with the protein having the amino acid sequence of SEQ ID NO: 1 (described in International Patent Publication WO03040370). Next, the membrane was washed twice with TBS buffer containing 0.05% Tween 20 for 5 minutes, and then shaken gently for 1 hour at room temperature with anti-rabbit IgG antibody labeled with alkaline phosphatase (manufactured by Bio-Rad) diluted 3,000 fold with TBS buffer containing 0.05% Tween 20 to carry out the second antibody reaction. Then, the membrane was washed twice with TBS buffer containing 0.05% Tween 20 for 5 minutes and then the coloring reaction was carried out by using AP coloring kit (manufactured by Bio-Rad). The membrane after coloring was kept after drying. By the above Western blotting method, in 26 of 40 recombinant tobacco individuals to which the plasmid pBI-NdG6-rSt-1609soy containing DNA having a nucleotide sequence encoding the amino acid sequence of SEQ ID NO: 1 has been introduced, it was detected relatively high amounts of the protein having molecular weight of 44 kDa. In 6 of 20 recombinant tobacco individuals to which the plasmid pBI-NdG6-rSt-1584soy containing DNA having a nucleotide sequence encoding the amino acid sequence of SEQ ID NO: 2 has been introduced, it was detected relatively high amounts of the protein having molecular weight of 44 kDa.

These recombinant tobacco individuals in which relatively high amounts of the protein of 44 kDa was detected were selected and seeds were harvested from the selected individuals to assay copy number of the introduced gene.

Example 3

Selection of a Recombinant Tobacco Line to which 1 Copy of the Cytochrome P450 Gene has been Introduced Based on the principle that a kanamycin resistant gene and a gene connected tandem to the resistant gene are linked when these genes are introduced into a plant by *Agrobacterium* method using a binary vector, from the recombinant tobacco individuals selected in Example 2, tobacco lines in which 1 copy of the introduced gene is located on one of homologous chromosomes were further selected.

The seeds were harvested from $T_0$ generation of the recombinant tobacco individuals selected in Example 2, and dipped in a 5-fold dilution of sodium hypochlorite solution (manufactured by Nacalai tesque) for 15 minutes for sterilization. About 50 seeds treated for sterilization were aseptically seeded on MS agar medium containing 100 mg/L kanamycin, and cultured at 25° C. in the light to germinate aseptically. After about 2 weeks, germinated seedlings were observed to select tobacco lines which indicate segregation rate of 3:1 at 5% significance level by chi-square test. As the results, of 26 lines selected in Example 2 from the recombinant tobacco individuals to which the plasmid pBI-NdG6-rSt-1609soy has been introduced, 9 lines were identified and selected as lines in which 1 copy of the introduced gene is located on one of homologous chromosomes. Of 6 lines selected in Example 2 from the recombinant tobacco individuals to which the plasmid pBI-NdG6-rSt-1584soy has been introduced, 2 lines were identified and selected as lines in which 1 copy of the introduced gene is located on one of homologous chromosomes.

Next, $T_1$-generation individuals of the above selected lines were transplanted to growing pots containing horicultural soil (Kureha Engei Baido manufactured by Kureha Chemical Industry Co. Ltd.), acclimated to the external environment in a growth chamber, then grown in a greenhouse. Flowers were covered with paper bags during flowering period to avoid crossing with other individuals, and seeds were harvested from them.

Example 4

Selection of Homozygote of the Recombinant Tobacco Line to Which the Cytochrome P450 Gene has been Introduced Seeds were harvested from the recombinant tobacco lines #17, #19, #22, #23, #25, #29, #30, #34 and #40 which were selected in Example 3 from among the lines to which the plasmid pBI-NdG6-rSt-1609soy has been introduced. Also, seeds were harvested from the recombinant tobacco lines #5 and #16 which were selected in Example 3 from among the lines to which the plasmid pBI-NdG6-rSt-1584soy has been introduced. Seeds of each 4 individuals of the lines #17 and #25 of the recombinant tobacco line into which the plasmid pBI-NdG6-rSt-1609soy has been introduced and the line #16 of the recombinant tobacco line to which the plasmid pBI-NdG6-rSt-1584soy has been introduced were seeded aseptically on MS agar medium containing 100 mg/L kanamycin according the method described in Example 3. An individual of which all seedlings show kanamycin resistance was selected as a homozygote.

Example 5

Spray Test of the Present Herbicidal Compound to the Recombinant Tobacco Line to Which a DNA Having a Nucleotide Sequence Encoding Amino Acid Sequence of SEQ ID NO: 1 or 2 has Been Introduced (ver. 1)

Seeds of the homozygote lines selected in Example 4 (seeds of lines #17 and #25 of the recombinant tobacco to which plasmid pBI-NdG6-rSt-1609soy has been introduced, and seeds of the line 1584soy#16 of the recombinant tobacco to which plasmid pBI-NdG6-rSt-1584soy has been introduced) were aseptically seeded on MS agar medium containing 100 mg/L kanamycin. Also, seeds of the wild-type tobacco line SR-1 were aseptically seeded on MS agar medium. After about 2 weeks, germinated seedlings were observed.

Germinated individuals were transplanted to growing pots containing horicultural soil (Kureha Engei Baido manufactured by Kureha Chemical Industry Co., Ltd.), acclimated to the external environment in a growth chamber, then grown for about 2 weeks at 23° C., 23 hours of day length in a growth chamber. Thus obtained plants were applied to the spray test of the present herbicidal compound, flufenpyr-ethyl.

Flufenpyr-ethyl was dissolved in Solvesso cocktail mixed Solvesso 200 (manufactured by Valent) and Sorpol 3816 (manufactured Sumitomo Chemical Co., Ltd.) at the ratio of 87.5:10 such that flufenpyr-ethyl was respectively contained 0.89 mg or 1.78 mg in 0.5 mL Solvesso cocktail. The spray liquid of flufenpyr-ethyl was prepared as the aqueous solution containing the Solvesso cocktail of 2.5% concentration in which the compound was dissolved and Agri dex of 1% concentration (manufactured by Valent) as adjuvant.

Spray of the spray liquid to the plant above described was carried out, by using running automatic spray machine (manufactured by Nambasekkei), such that spray liquid 20 mL was sprayed to the recombinant tobacco seedlings put at 0.9 square meter of the sprayed area in a uniform way. After about 2 weeks, the sensitivity of the applied recombinant tobacco line to flufenpyr-ethyl was compared to the sensitivity of the wild-type tobacco line SR-1 to flufenpyr-ethyl. In the above spray test, 4 individuals of the recombinant tobacco were used with respect to each applied amount of flufenpyr-ethyl. The sensitivity of the recombinant tobacco to flufenpyr-ethyl was decided by scoring it based on the index below, and calculating the average of the score of 4 individuals with respect to each recombinant tobacco line and applied amount for it. The same spray test of wild-type line SR-1 was carried out as a negative control. The results are shown in Table 1.

<Scoring Index Based on the Degree of Phytotoxicity as Dying of the Individual and Browning or Whitening of the Leaves or Stems Caused by Compound Spraying>

"0": the case in that the individual was died;

"1": the case in that phytotoxicity as browning or whitening of the leaves or stems was caused, and the phytotoxicity seriously affect the individual's growth, but it was not died;

"2": the case in that phytotoxicity as browning or whitening of the leaves or stems was caused, but the phytotoxicity did not seriously affect the individual's growth, but it was not died; and "3": the case in that phytotoxicity as browning or whitening of the leaves or stems was small, or almost not observed.

TABLE 1

| | Applied amount of flufenpyr-ethyl (mg/20 mL spray liquid) | |
|---|---|---|
| Applied tobacco line | 0.89 | 1.78 |
| wild type SR-1 (negative control) | 1.7 | 0.0 |
| 1609soy#17 (the present plant) | 3.0 | 3.0 |
| 1609soy#25 (the present plant) | 3.0 | 3.0 |
| 1584soy#16 (the present plant) | 3.0 | 3.0 |

Figure 3:
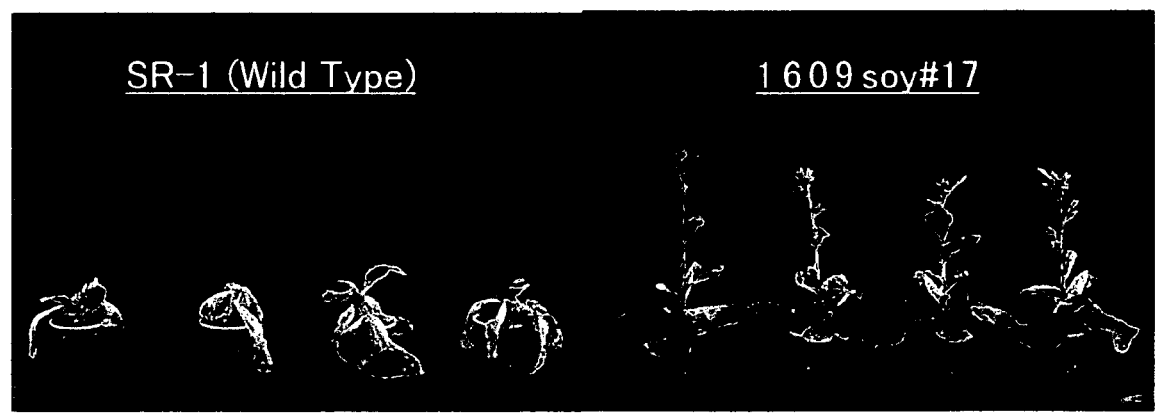
FIG. 3 shows the photos of the wild-type line SR-1 and the present plant (line 1609soy#17) grown for 14 days in a greenhouse after spraying flufenpyr-ethyl (applied amount 1.78 mg/20 mL spray liquid).

The photos of the wild-type line SR-1 and the plants of the Invention (line 1609soy#17) grown for 14 days in a greenhouse after spraying flufenpyr-ethyl (applied amount 1.78 mg/20 mL spray liquid) are shown in FIG. 3.

Example 6

Spray Test of the Present Herbicidal Compound to the Recombinant Tobacco Line to Which a DNA Having a Nucleotide Sequence Encoding the Amino Acid Sequence of SEQ ID NO: 1 has been Introduced (ver. 2)

As to the homozygote line 1609soy#25 selected in Example 4 from among the recombinant tobacco lines to which a DNA having a nucleotide sequence encoding the amino acid sequence of SEQ ID NO: 1 has been introduced, and the wild-type tobacco line SR-1, their sensitivities to the compound (I), carfentrazone-ethyl and sulfentrazone were investigated according to the method described in Example 5 (evaluation by scoring index based on the degree of phytotoxicity as dying of the individual and browning or whitening of the leaves or stems caused by compound spraying).

Each spray liquid of the above herbicidal compounds was prepared as follows.

(1) In the case of the compound (I): according to the method described in Example 5, the spray liquid was prepared such that 0.089 mg, 0.223 mg or 0.446 mg of the compound (I) was contained in the spray liquid.

(2) In the case of carfentrazone-ethyl: the spray liquid was prepared by dissolving dry flowable preparation of carfentrazone-ethyl (AIM™ HERBICIDE manufactured by FMC, containing 40#(w/w) of carfentrazone-ethyl) with Agri dex (manufactured by Valent) 1% aqueous solution to be contained 0.446 mg, 0.893 mg or 4.46 mg of carfentrazone-ethyl in the spray liquid.

(3) In the case of sulfentrazone: the spray liquid was prepared by dissolving dry flowable preparation of sulfentrazone (Cover™ 75DF manufactured by FMC, containing 75% (w/w) of sulfentrazone) in Agri dex (manufactured by Valent) 1% aqueous solution to be contained 0.446 mg, 0.893 mg, 1.78 mg or 4.46 mg of sulfentrazone in the spray liquid.

As the results, in the plant (line 1609soy#17) to which the above each herbicidal compound was applied, the phytotoxicity was reduced and remarkable improvement of the resistance was recognized as compared to the wild type line SR-1 (negative control). The results of the spray test of carfentrazone-ethyl are shown in Table 2.

TABLE 2

| Applied tobacco line | Applied amount of carfentrazone-ethyl (mg/20 mL spray liquid) | | |
|---|---|---|---|
| | 0.446 | 0.893 | 4.46 |
| wild type SR-1 (negative control) | 1.0 | 0.0 | 0.0 |
| 1609soy#25 (the present plant) | 2.5 | 1.8 | 1.5 |

Example 7

Figure 4:
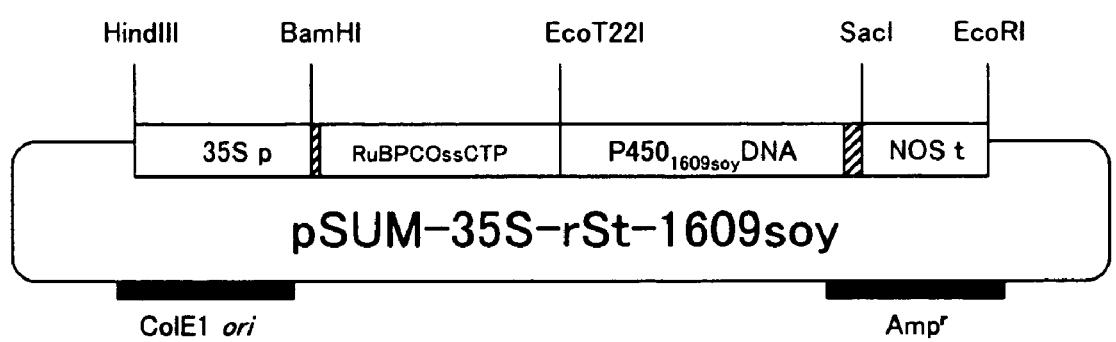
FIG. 4 shows the restriction map of the plasmid pBI-35S-rSt-1609soy.
Figure 5:
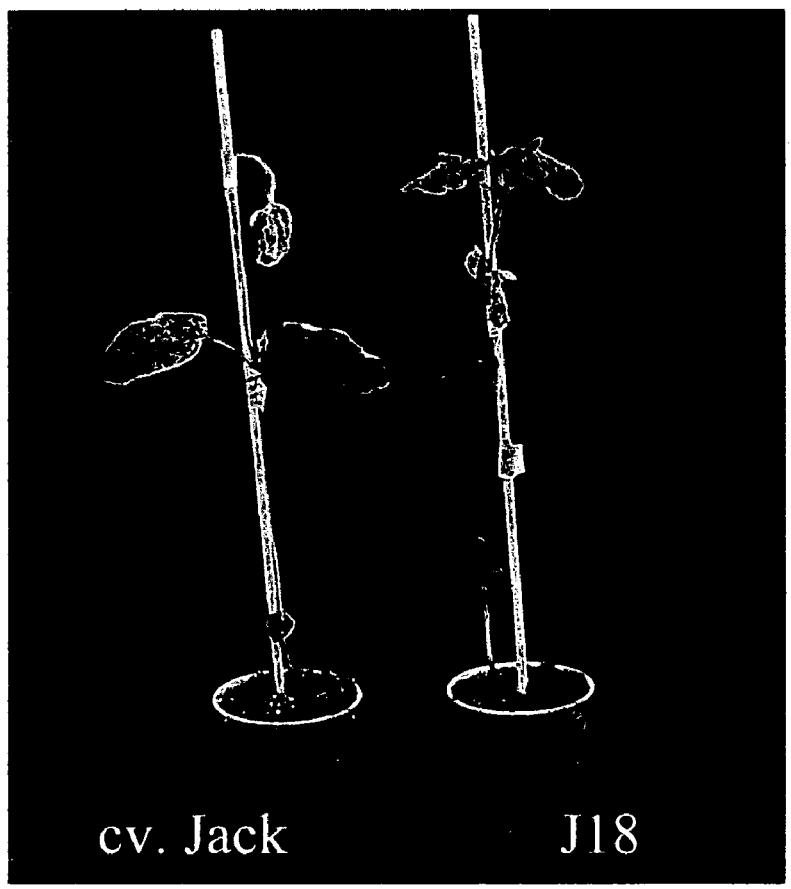
FIG. 5 shows the photos of the wild-type line cv. Jack and the present plant (the recombinant soybean line J18) grown for 15 days in a greenhouse after spraying carfentrazone-ethyl (applied amount 3.57 mg/20 mL spray liquid).

Spray Test of the Present Herbicidal Compound to the Recombinant Soybean Line to which a DNA Having a Nucleotide Sequence Encoding the Amino Acid Sequence of SEQ ID No: 1 has been Introduced By digesting plasmid pUCrSt1609soy described in Example 75 of WO0304370 which contains a DNA having a nucleotide sequence encoding the amino acid sequence of SEQ ID NO: 1 with restriction enzymes Bam HI and Sac I, the DNA containing the nucleotide sequence encoding the amino acid sequence of SEQ ID NO: 1 was isolated. By inserting the DNA between Bam HI cleavage site and Sac I cleavage site of plasmid pBI221 (manufactured by Clontech. GenBank Association Number: AF502128), plasmid pSUM-35S-rSt-1609soy (FIG. 4) was constructed wherein the chimeric DNA, in which the above DNA was connected in frame of codons immediately after the nucleotide sequence encoding the chloroplast transit peptide of soybean (cv. Jack) RuBPC small subunit, was connected downstream of 35S promoter of cauliflower mosaic virus. The plasmid pSUM-35S-rSt-1609soy, and hygromycin selective marker plasmid containing a DNA in which APH4 gene derived from E. coli (GenBank Accession Number; V01499) was connected downstream of the promoter derived from plasmid pG8CRG1-2 described in EP0976832, were mixed at the ratio of 1:1 and introduced into soybean raspberry-shaped somatic embryo according to the method described in Example 75 of WO0304370. By selecting the soybean raspberry-shaped somatic embryo on a selection medium containing hygromycin according to the method described in Example 47 of WO0304370, it was obtained 155 lines of soybean raspberry-shaped somatic embryos being able to grow on the selection medium and containing a chromosome to which the DNA having the nucleotide sequence encoding the amino acid sequence of SEQ ID NO: 1 has been introduced.

By PCR method described below, it was confirmed that the DNA having the nucleotide sequence encoding the amino acid sequence of SEQ ID NO: 1 was introduced into chromosome of the selected somatic embryo. After sampling the somatic embryo selected on the selection medium, 40 μL PrepMan Ultra Reagent (manufactured by Applied Biosystems) was added thereto. The obtained mixture was heated at 100° C. for 10 minutes, and then cooled. By centrifuging the cooled mixture at 15,000 rpm for 1 minute, the supernatant was obtained. The obtained supernatant was used as chromosomal DNA solution to be a template in the following PCR reaction. Using 1 μL of the chromosomal DNA solution as the template, and DNA polymerase Ex-Taq-HS (manufactured by TAKARA BIO INC.), total 20 μL of the reaction mixture was prepared according to the attached protocol. The prepared reaction mixture was kept at 94° C. for 2 minutes, and repeated 30 times the cycle which was a set of the steps to keep at 94° C. for 30 seconds, then at 58° C. for 30 seconds, then at 72° C. for 1 minute, and finally kept at 72° C. for 2 minutes. As the primers, two kinds of the synthetic oligonucleotide (SEQ ID NO: 3 and SEQ ID NO: 4) were used. 10 μL of the reaction mixture after the reaction was applied to the electrophoresis using an agarose gel containing 1.5% agarose in TBE buffer, and then stained the agarose gel with ethidium bromide to detect under the irradiation of 254 nm of ultraviolet a 503 bp DNA amplified in the above PCR reaction. As the results, it was confirmed that the DNA having the nucleotide sequence encoding the amino acid sequence of SEQ ID NO: 1 was introduced.

From the selected somatic embryos, the individuals were regenerated according to the method described in Example 47 of WO0304370. The concentration of agar in the development medium was 1.0 (w/v)%. The individual plant lets rooting and developing leaves were acclimated to the external environment in a growth chamber and then grown in a greenhouse according to the methods described in Example 47 of WO0304370. Seeds were harvested from the fertile individuals. Thus, 79 lines of the recombinant soybean to which pSUM-35S-rSt-1609soy has been introduced was obtained. Leaves were sampled from the individuals, and 20 lines of the recombinant soybean in which the 44 kDa protein having the amino acid sequence of SEQ ID NO: 1 was accumulated in leaves thereof were selected according to the method described in Example 2. Among them, it was detected relatively high amounts of the protein in the lines J16, J18, J26 and J28.

Seeds of these lines were seeded and grown in growing pots containing horicultural soil (Kureha Engei Baido manufactured by Kureha Chemical Industry Co. Ltd.) When trifoliate leaves were developed after germination, the seedlings were transplanted to growing pots containing the soil prepared by mixing equal amount of the Kureha Engei Baido and field soil, and then grown in a greenhouse according to the method of Example 17 of WO0304370 to obtain seeds of $T_2$ generation of each line. Among the obtained $T_2$ generations, seeds of $T_2$ generation of the line J18 (seeds of the recombinant soybean) were seeded in growing pots containing horicultural sail (Kureha Engei Baido manufactured by Kureha Chemical Industry Co., Ltd.) and grown. According to the above method described in Example 5, it was sprayed carfentrazone-ethyl to the seedling on the $21^{st}$ day after seeding, and compared the sensitivity to carfentrazone-ethyl of the recombinant soybean with the sensitivity to carfentrazone-ethyl of wild-type soybean line (cv. Jack) at 2 weeks after spraying. The spray liquid of the above herbicidal compound was prepared as follows.

(The Spray Liquid of the Present Herbicidal Compound)

The spray liquid was prepared by diluting dry flowable preparation of carfentrazone-ethyl (AIM™ HERBICIDE manufactured by FMC, containing 40% (w/w) of carfentrazone-ethyl) with Agri dex (manufactured by Valent) 1% aqueous solution to be contained 1.79 mg, 3.57 mg or 7.14 mg of carfentrazone-ethyl in the spray liquid.

The sensitivity of the recombinant soybean to carfentrazone-ethyl was decided by scoring it based on the index below, and calculating the average of the scores with respect to each recombinant soybean line and applied amount for it. The same spray test of the wild-type soybean line (cv. Jack) was carried out as a negative control.

As the results, in the present plant (line J18) to which the above herbicidal compound was applied, the phytotoxicity was reduced and remarkable improvement of the resistance was recognized as compared to the wild-type plant cv. Jack (negative control). The results of the spray test of carfentrazone-ethyl are shown in Table 3.

<Scoring Index Based on the Degree of Phytotoxicity as Dying of the Individual and Browning or Whitening of the Leaves or Stems Caused by Compound Spraying>

"0": the case in that the individual was died;

"1": the case in that phytotoxicity as browning or whitening of the leaves or stems was caused, and the phytotoxicity seriously affect the individual's growth, but it was not died;

"2": the case in that phytotoxicity as browning or whitening of the leaves or stems was caused, but the phytotoxicity did not seriously affect the individual's growth, but it was not died; and "3": the case in that phytotoxicity as browning or whitening of the leaves or stems was small, or almost not observed.

TABLE 3

| | Applied amount of carfentrazone-ethyl (mg/20 mL spray liquid) | | | |
|---|---|---|---|---|
| Applied soybean line | 0 | 1.79 | 3.57 | 7.14 |
| wild type cv. Jack (negative control) | 3.0 | 1.0 | 0.9 | 0.3 |
| J18 (the present plant) | 3.0 | 1.8 | 1.4 | 0.9 |

The photos of the wild-type line cv. Jack and the present plant (the recombinant soybean line J18) grown for 15 days in a greenhouse after spraying carfentrazone-ethyl (applied amount 3.57 mg/20 mL spray liquid) are shown in FIG. 5.

Free text in Sequence Listing

SEQ ID No: 3

Designed Oligonucleotide Primer for PCR

SEQ ID No: 4

Designed Oligonucleotide Primer for PCR

What is claimed is:

1. A method for controlling weeds comprising applying one or more compounds selected from the group consisting of:
   (1) flufenpyr-ethyl,
   (2) 2-[4-chloro-2-fluoro-5-(2-propynyloxy)phenyl]-4-methy-5-(trifluoromethyl)-3(2H)-pyridazinone,
   (3) carfentrazone-ethyl, and
   (4) sulfentrazone;
   to a cultivation area of a plant that expresses an introduced DNA encoding cytochrome P450 selected from the group consisting of:
   (a) cytochrome P450 having activity of metabolizing a protoporphyrinogen IX oxidase inhibitory-type herbicidal compound and comprising an amino acid sequence that has 90% or more sequence homology to the amino acid sequence of SEQ ID NO: 1 or 2,
   (b) cytochrome P450 comprising the amino acid sequence of SEQ ID NO: 1, and
   (c) cytochrome P450 comprising an amino acid sequence of SEQ ID NO: 2.

2. A method for selecting a herbicidal compound resistant plant, comprising:
   1) applying or adding one or more compounds selected from the group consisting of:
      (1) flufenpyr-ethyl,
      (2) 2-[4-chloro-2-fluoro-5-(2-propynyloxy)phenyl]-4-methy-5-(trifluoromethyl)-3(2H)-pyridazinone,
      (3) carfentrazone-ethyl, and
      (4) sulfentrazone;
      to a cultivation area of a plant that expresses an introduced DNA encoding cytochrome P450 selected from the group consisting of:
      (a) cytochrome P450 having activity of metabolizing a protoporphyrinogen IX oxidase inhibitory-type herbicidal compound and comprising an amino acid sequence that has 90% or more sequence homology to the amino acid sequence of SEQ ID NO: 1 or 2,
      (b) cytochrome P450 comprising the amino acid sequence of SEQ ID NO: 1, and
      (c) cytochrome P450 comprising the amino acid sequence of SEQ ID NO: 2 ; and
   2) selecting a plant which has survived the weed control effect of said applied or added compounds.

3. The method according to claim 1, wherein flufenpyr-ethyl is applied to the cultivation area of the plant.

4. The method according to claim 1, wherein 2-[4-chloro-2-fluoro-5-(2-propynyloxy)phenyl]-4-methy-5-(trifluoromethyl)-3(2H)-pyridazinone is applied to the cultivation area of the plant.

5. The method according to claim 1, wherein carfentrazone-ethyl is applied to the cultivation area of the plant.

6. The method according to claim 1 wherein sulfentrazone is applied to the cultivation area of the plant.

* * * * *

UNITED STATES PATENT AND TRADEMARK OFFICE
CERTIFICATE OF CORRECTION

| | | |
|---|---|---|
| PATENT NO. | : 7,521,596 B2 | Page 1 of 1 |
| APPLICATION NO. | : 11/129574 | |
| DATED | : April 21, 2009 | |
| INVENTOR(S) | : Matsushima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this

Nineteenth Day of October, 2010

David J. Kappos
*Director of the United States Patent and Trademark Office*